United States Patent
Oh et al.

(10) Patent No.: US 12,012,379 B2
(45) Date of Patent: Jun. 18, 2024

(54) METHOD OF PURIFYING ALPHA-OLEFIN AND COMPOSITION FOR PURIFYING ALPHA-OLEFIN THEREFOR

(71) Applicant: SABIC SK NEXLENE COMPANY PTE. LTD., Singapore (SG)

(72) Inventors: Yeonock Oh, Daejeon (KR); Choon Sik Shim, Sejong-si (KR); Dae Ho Shin, Daejeon (KR); Jaesuk Choi, Daejeon (KR); Howon Lee, Daejeon (KR)

(73) Assignee: SABIC SK NEXLENE COMPANY PTE. LTD., Singapore (SG)

( * ) Notice: Subject to any disclaimer, the term of this patent is extended or adjusted under 35 U.S.C. 154(b) by 228 days.

(21) Appl. No.: 17/757,355

(22) PCT Filed: Dec. 8, 2020

(86) PCT No.: PCT/IB2020/061619
§ 371 (c)(1),
(2) Date: Jun. 14, 2022

(87) PCT Pub. No.: WO2021/124008
PCT Pub. Date: Jun. 24, 2021

(65) Prior Publication Data
US 2023/0032361 A1    Feb. 2, 2023

(30) Foreign Application Priority Data
Dec. 18, 2019    (KR) .................. 10-2019-0169339

(51) Int. Cl.
*C07C 7/13*    (2006.01)
*C08F 6/00*    (2006.01)
*C08F 10/08*   (2006.01)
*C08F 10/14*   (2006.01)

(52) U.S. Cl.
CPC .............. *C07C 7/13* (2013.01); *C08F 6/005* (2013.01); *C08F 10/08* (2013.01); *C08F 10/14* (2013.01)

(58) Field of Classification Search
CPC ........... C07C 7/13; C07C 11/02; C07C 11/08; C07C 11/10; C07C 11/107; C08F 6/005; C08F 10/08; C08F 10/14; C08F 10/00; C08F 6/001; B01D 15/02; B01J 20/08; B01J 20/18; B01J 20/20; B01J 20/2816; B01J 20/28052; B01J 20/28066; B01J 20/28069; B01J 20/28088; B01J 20/3007; B01J 20/28073; B01J 20/28083
See application file for complete search history.

(56) References Cited

U.S. PATENT DOCUMENTS

| | | | | |
|---|---|---|---|---|
| 6,124,410 A * | 9/2000 | Ito | ............ | C08F 10/00 526/127 |
| 6,492,568 B1 * | 12/2002 | Murray | ............... | C07C 7/14841 568/909 |
| 6,653,514 B1 * | 11/2003 | Murray | .................. | C07C 29/16 585/329 |
| 8,664,153 B1 * | 3/2014 | Ahumada | ............ | B01J 20/3204 502/417 |
| 9,714,204 B1 * | 7/2017 | Drew | ......................... | C10J 3/72 |
| 2008/0107589 A1 * | 5/2008 | von Blucher | ............ | B01J 20/20 423/449.1 |
| 2008/0139857 A1 | 6/2008 | Henn et al. | | |
| 2008/0207443 A1 * | 8/2008 | Gadkaree | ............. | B01J 20/0218 502/417 |
| 2009/0111690 A1 * | 4/2009 | Gadkaree | .......... | B01J 20/28042 502/417 |
| 2010/0173772 A1 * | 7/2010 | Robinson | ........... | B01J 20/28023 502/402 |
| 2011/0020202 A1 * | 1/2011 | Gadkaree | .......... | B01J 20/28042 502/185 |
| 2011/0073527 A1 | 3/2011 | Jan et al. | | |
| 2012/0118160 A1 | 5/2012 | Heffes et al. | | |
| 2016/0347690 A1 | 12/2016 | Peitz et al. | | |
| 2017/0232422 A1 * | 8/2017 | Romig | ................. | B01J 20/3433 502/34 |
| 2018/0170760 A1 | 6/2018 | Tsukazaki et al. | | |
| 2018/0296969 A1 * | 10/2018 | Awadh | ................. | B01J 20/0237 |
| 2019/0291073 A1 | 9/2019 | Hanamoto et al. | | |
| 2019/0336906 A1 | 11/2019 | Ji et al. | | |
| 2020/0018265 A1 * | 1/2020 | Chen | .................. | B01J 20/28026 |
| 2020/0368670 A1 * | 11/2020 | Santana | ............ | B01D 53/0462 |
| 2022/0023829 A1 * | 1/2022 | Ozdemir | ............ | B01J 20/28083 |
| 2022/0212161 A1 * | 7/2022 | Alden | ................ | F02M 25/0854 |

(Continued)

FOREIGN PATENT DOCUMENTS

DE    1187603 B    2/1965
DE    69503185 T2    12/1998
(Continued)

OTHER PUBLICATIONS

ISA Korean Intellectual Property Office, International Search Report Issued in Application No. PCT/IB2020/061619, Mar. 11, 2021, WIPO, 3 pages.

(Continued)

*Primary Examiner* — Ali Z Fadhel

(74) *Attorney, Agent, or Firm* — McCoy Russell LLP

(57) ABSTRACT

Provided are a method of purifying an alpha-olefin and a composition for purifying an alpha-olefin therefor. More specifically, a method of purifying an alpha-olefin having an excellent effect of removing impurities in the alpha-olefin and a composition for purifying an alpha-olefin therefor are provided.

11 Claims, No Drawings

(56) References Cited

U.S. PATENT DOCUMENTS

2022/0213391 A1\* 7/2022 Koseoglu ............. C10G 25/003
2023/0026065 A1\* 1/2023 Otsuka ................ B01J 20/2808

FOREIGN PATENT DOCUMENTS

| DE | 19934144 A1 | 2/2001 |
|----|----|----|
| DE | 102005026213 A1 | 12/2006 |
| EP | 1918022 A1 | 5/2008 |
| RU | 2152421 C1 | 7/2000 |
| SU | 245964 A1 | 7/1976 |
| WO | 0185653 A1 | 11/2001 |

OTHER PUBLICATIONS

Federal Institute of Industrial Property, Search Report Issued in Application No. 2022119196, Feb. 10, 2023, 4 pages.
Federal Institute of Industrial Property, Office Action Issued in Application No. 2022119196, Feb. 10, 2023, 9 pages.
European Patent Office, Extended European Search Report Issued in Application No. 20903890.0, Jan. 5, 2024, Germany, 10 pages.

\* cited by examiner

METHOD OF PURIFYING ALPHA-OLEFIN AND COMPOSITION FOR PURIFYING ALPHA-OLEFIN THEREFOR

CROSS REFERENCE TO RELATED APPLICATIONS

The present application is a U.S. National Phase of International Application No. PCT/IB2020/061619 entitled "METHOD OF PURIFYING ALPHA-OLEFIN AND COMPOSITION FOR PURIFYING ALPHA-OLEFIN THEREFOR," and filed on Dec. 8, 2020. International Application No. PCT/IB2020/061619 claims priority to Korean Patent Application No. 10-2019-0169339 filed on Dec. 18, 2019. The entire contents of each of the above-listed applications are hereby incorporated by reference for all purposes.

TECHNICAL FIELD

The following disclosure relates to a method of purifying an alpha-olefin and a composition for purifying an alpha-olefin therefor. More specifically, the following disclosure relates to a method of purifying an alpha-olefin having an excellent effect of removing impurities in the alpha-olefin and a composition for purifying an alpha-olefin therefor.

BACKGROUND

In general, an alpha-olefin contains impurities produced during an oligomerization process or a polyolefin polymerization process. Typical impurities include residues from a catalyst used in polymerization, for example, a cocatalyst, a remover, an oligomer, a by-product, various volatile low-molecular weight compounds, and the like. The impurities may have an adverse effect, even in the case of being contained only at a low concentration in a polymer.

As an example, a polymer used in a water pipe may cause deterioration of taste or odor of water to be carried. In addition, it is difficult for a film used in an electric apparatus to escape electrical breakthrough when the film contains metal impurities. In addition, a polymer used in automotive applications may cause a fogging problem when a volatile compound volatilizes and is condensed on a car window, and simultaneously, deteriorates an exterior of an interior part.

In particular, among the impurities present in an alpha-olefin, an amine-based material is strongly adsorbed to an adsorbent and is not regenerated in a regeneration process to cause pore loss, thereby significantly reducing a long-term purification ability.

A method of dramatically preventing deterioration of a purification ability of an adsorbent and significantly improving a purification ability for removing an amine-based material in an alpha-olefin, is currently needed.

SUMMARY

An embodiment of the present invention is directed to providing a method of purifying an alpha-olefin which may significantly improve an effect of removing impurities in the alpha-olefin and a composition for purifying an alpha-olefin.

In particular, a method of purifying an alpha-olefin having excellent purification selectivity to an amine-based material in impurities and a composition for purifying an alpha-olefin are provided.

Another embodiment of the present invention is directed to providing a method of purifying an alpha-olefin which may express a long-term purification effect by dramatically preventing a long-term decrease in an impurity purification ability and a composition for purifying an alpha-olefin.

In one general aspect, in a method of purifying an alpha-olefin, impurities are removed by a combination of molded activated carbon having a specific surface area of 1,200 $m^2/g$ or more, an average particle diameter of 0.8 to 40 mm, and a pore volume of more than 0.6 $cm^3/g$ as measured by a nitrogen adsorption method, in which pores having a diameter of 2 nm or more account for 60% or more of the total pores; and an alumina-zeolite composite.

The method of purifying an alpha-olefin according to an exemplary embodiment of the present invention may be performed during a poly-alpha-olefin polymerization reaction or an ethylene oligomerization reaction.

Preferably, according to an exemplary embodiment of the present invention, the method of purifying an alpha-olefin may be performed during the poly-alpha-olefin polymerization reaction.

The method of purifying an alpha-olefin according to an exemplary embodiment of the present invention may include treatment with the activated carbon and then treatment with the alumina-zeolite composite.

According to an exemplary embodiment of the present invention, the activated carbon and the alumina-zeolite composite may be included at a weight ratio of 1:1 to 1:20.

The alumina-zeolite composite according to an exemplary embodiment of the present invention may include 50 to 95 wt % of alumina and 5 to 50 wt % of zeolite.

According to an exemplary embodiment of the present invention, the alpha-olefin is any one or a mixture of two or more selected from 1-butene, 1-pentene, 1-hexene, 4-methyl-1-pentene, 1-octene, 1-decene, 1-dodecene, and the like.

Preferably, according to an exemplary embodiment of the present invention, the alpha-olefin may be any one or a mixture of two or more selected from 1-hexene, 1-octene, and the like.

The impurities according to an exemplary embodiment of the present invention may be an amine-based compound.

In another general aspect, a composition for purifying an alpha-olefin includes: molded activated carbon having a specific surface area of 1,200 $m^2/g$ or more, an average particle diameter of 0.8 to 40 mm, and a pore volume of more than 0.6 $cm^3/g$ as measured by a nitrogen adsorption method, in which pores having a pore diameter of 2 nm or more account for 60% or more of the total pores; and an alumina-zeolite composite.

The composition for purifying an alpha-olefin according to an exemplary embodiment of the present invention may be a two agent-type composition including the activated carbon as a first agent and the alumina-zeolite composite as a second agent.

Other features and aspects will be apparent from the following detailed description and the claims.

DETAILED DESCRIPTION

Hereinafter, the present invention will be described in more detail with reference to specific examples and exemplary embodiments. However, the following specific examples or exemplary embodiments are only a reference for describing the present invention in detail, and the present invention is not limited thereto, and may be implemented in various forms.

In addition, unless otherwise defined, all technical terms and scientific terms have the same meanings as those commonly understood by a person skilled in the art to which the present invention pertains. The terms used herein are only for effectively describing a certain specific example, and are not intended to limit the present invention.

Throughout the present specification describing the present invention, unless explicitly described to the contrary, "comprising" any elements will be understood to imply further inclusion of other elements rather than the exclusion of any other elements.

In addition, the singular form used in the specification and claims appended thereto may be intended to also include a plural form, unless otherwise indicated in the context.

Since an alpha-olefin contains impurities produced by a nitrogen component derived from crude oil, it was difficult to produce or provide a pure alpha-olefin without impurities by a conventional purification technique.

In order to solve the problem, the inventors of the present invention found that a purification method having significantly improved removal efficiency of nitrogen-containing impurities by a combination of specific constitutional components and a specific method may be provided, thereby completing the present invention.

The method of purifying an alpha-olefin according to the present invention is specifically as follows.

The method of purifying an alpha-olefin according to the present invention removes impurities by a combination of molded activated carbon having a specific surface area of 1,200 m$^2$/g or more, an average particle diameter of 0.8 to 40 mm, and a pore volume of more than 0.6 cm$^3$/g as measured by a nitrogen adsorption method, in which pores having a pore diameter of 2 nm or more account for 60% or more of the total pores; and an alumina-zeolite composite.

By using the combination of specific activated carbon and an alumina-zeolite composite, impurities, in particular, the nitrogen-containing impurities may be removed with significantly excellent efficiency.

In addition, as an exemplary embodiment, in the activated carbon, a pore volume measured by a nitrogen adsorption method may be more than 0.6 cm$^3$/g and pores having a pore diameter of more than 2 nm may account for 60% or more of the total pores. More specifically, the pore volume may be more than 0.6 cm$^3$/g and pores having a pore diameter of 2 nm or more may account for 60 to 99% of the total pores. Within the range, adsorption efficiency of the nitrogen-containing impurities may be more improved.

According to an exemplary embodiment of the present invention, the method of purifying an alpha-olefin may be provided in various processes. Specifically, for example, the method may be used in any one or two or more processes selected from a process for purifying an alpha-olefin, a process for producing an alpha-olefin, a process for polymerizing an alpha-olefin, a process for recycling an alpha-olefin, a process for recovering an alpha-olefin, and the like, but the process is not limited thereto as long as it is a process including an alpha-olefin.

According to an exemplary embodiment of the present invention, the method of purifying an alpha-olefin may be performed at any one or two or more positions selected from an introduction unit, a reaction unit, a circulation unit, a recovery unit, and the like in a process including an alpha-olefin.

Specifically, for example, the introduction unit means a path for a reactant to move into an inside of a reactor, and the reaction unit may mean a reactor in which the reactant performs polymerization or synthesis. In addition, the circulation unit means a circulation path for reintroducing a residual material in the reactant, and the recovery unit means a path for a final material after the reaction to be discharged.

Preferably, according to an exemplary embodiment of the present invention, impurities are present in the alpha-olefin, and when the purification method is installed or added to the path including the alpha-olefin, an impurity purification ability may be dramatically improved. For example, when the alpha-olefin is provided as a monomer, the purification method may be installed or added at any one or two or more positions selected from the introduction unit, the reaction unit, the circulation unit, and the like. As another example, when the alpha-olefin is produced, the purification method may be installed or added at any one or two or more positions selected from the reaction unit, the circulation unit, the recovery unit, and the like.

Specifically, according to an exemplary embodiment of the present invention, the method of purifying an alpha-olefin may be performed during a poly-alpha-olefin polymerization reaction to which the alpha-olefin is added as a monomer or an ethylene oligomerization reaction in which the alpha-olefin is produced. By purifying the impurities by the method of purifying an alpha-olefin during the reaction in which the alpha-olefin is provided or produced as described above, a high-purity alpha-olefin may be provided, and performance deterioration due to the impurities may be prevented in various fields to be provided. Furthermore, due to a long-term purification ability, a dramatic impurity purification effect may be implemented.

According to an exemplary embodiment of the present invention, the method of purifying an alpha-olefin may be performed during a poly-alpha-olefin polymerization reaction or an ethylene oligomerization reaction, and specifically, may be performed in any one or two or more steps selected from before the reaction, during the reaction, and after the reaction. Specifically, for example, the purification method may be performed before the polymerization reaction of poly-alpha-olefin or after the ethylene oligomerization reaction. Preferably, in order to implement an excellent effect of purifying impurities, in particular, the nitrogen-containing impurities, the purification method may be performed before a poly-alpha-olefin polymerization reaction.

According to an exemplary embodiment of the present invention, in the method of purifying an alpha-olefin, the alpha-olefin may be treated with a mixture of the activated carbon and the alumina-zeolite composite, or treated with each of them sequentially, for impurity purification. Preferably, the alpha-olefin may be treated with the alumina-zeolite composite after being treated with the activated carbon, sequentially. As described above, after impurity purification is first performed by the activated carbon as a guard bed, additional impurity purification is performed by the alumina-zeolite composite, thereby implementing a significantly improved impurity purification effect. Furthermore, a problem that the impurities are adsorbed to the inside of the alumina-zeolite composite and is not removed is prevented, thereby implementing a long-term purification ability.

The activated carbon according to the present invention is molded activated carbon having a specific surface area of 1,200 m$^2$/g or more and an average particle diameter of 0.8 to 40 mm. Preferably, the activated carbon may be molded activated carbon having the specific surface area of 1,200 to 3,000 m$^2$/g and the average particle diameter of 0.8 to 30 mm. More preferably, the activated carbon may be molded activated carbon having the specific surface area of 1,200 to 2,500 m²/g and the average particle diameter of 0.85 to 20 mm. Here, the molded activated carbon means a porous particle form formed by agglomerating fine powder. In addition, the activated carbon may have a pore volume of more than 0.6 cm³/g as measured by a nitrogen adsorption method and pores having a pore diameter of more than 2 nm accounting for 60% or more, and more preferably 60 to 99% of the total pores.

When the activated carbon satisfying the physical properties as described above is provided, an effect of purifying impurities in the alpha-olefin is excellent and, in particular, adsorption selectivity of nitrogen-containing impurities is good. More specifically, an effect that a removal rate of nitrogen-containing impurities is 85% or more, more specifically 85% to 99.9%, and more preferably 87% to 98% may be shown. This may improve removal efficiency of the nitrogen-containing impurities by 3 times or more, specifically 3 times to 5 times, as compared with the case of not using the activated carbon.

In addition, such effect may be expressed by using the alumina-zeolite composite in combination.

When the activated carbon has a specific surface area of less than 1,200 m²/g, adsorption capacity is significantly low, so that it is difficult to remove impurities in the alpha-olefin. Furthermore, selectivity to the impurities such as moisture and other hydrocarbons is higher than the selectivity to the nitrogen-containing impurities and purification performance and a lifespan may be decreased.

In addition, when the activated carbon has an average particle diameter of less than 0.8 mm or more than 40 mm, it is difficult to adsorb impurities, and in particular, the selectivity to the nitrogen-containing impurities is decreased, thereby deteriorating purification performance of the alumina-zeolite composite provided later.

In addition, when the activated carbon is provided as a powder form instead of the molded activated carbon, the average particle diameter and a pore distribution may be satisfied, but additional process costs due to pressure loss, separation of a rear end of a purification tower, and the like are caused, and thus, economic feasibility is significantly lowered.

According to an exemplary embodiment of the present invention, the alumina-zeolite composite may be a composite of alumina and zeolite, and specifically a formulation of the same kind of modified activated alumina and a zeolite molecular sieve adsorbent.

The alumina-zeolite composite according to the present invention is not limited, but specifically, for example, is a bead form having a crush strength of 10 to 60 N and an average particle diameter of 1.0 to 5.0 mm. Preferably, the alumina-zeolite composite may be a bead form having the crush strength of 20 to 60 N and the average particle diameter of 1.0 to 4.5 mm. More preferably, the alumina-zeolite composite may be a bead form having the crush strength of 30 to 60 N and the average particle diameter of 1.3 to 4.5 mm. Here, the bead means a shape in which the composite itself forms particles in a bead form. The crush strength is measured in accordance with ASTM D3102-72.

When the alumina-zeolite composite satisfying the physical properties is provided, an effect of purifying impurities in the alpha-olefin is excellent, a purification ability is not deteriorated even in the case of exposure to an excessive amount of impurities, and an excellent purification effect may be expressed. Such effect may be expressed by constituting the activated carbon together.

In addition, when the alumina-zeolite composite has an average particle diameter of less than 1.0 mm or more than 5.0 mm, it is difficult to adsorb impurities, and in particular, long-term durability to a purification ability and a lifespan may be decreased due to strong adsorption of the nitrogen-containing impurities.

In addition, when the alumina-zeolite composite is not a bead form but a powder form, the crush strength and the average particle diameter as described above may not be satisfied and the impurity purification effect is significantly decreased.

According to an exemplary embodiment of the present invention, the alumina-zeolite composite may include 50 to 95 wt % of alumina and 5 to 50 wt % of zeolite. Preferably, the alumina-zeolite composite may include 85 to 90 wt % of alumina and 10 to 15 wt % of zeolite, but is not limited thereto.

According to an exemplary embodiment of the present invention, the activated carbon and the alumina-zeolite composite may be included at a weight ratio of 1:1 to 1:20. Preferably, the weight ratio may be 1:5 to 1:20. When the activated carbon and the alumina-zeolite composite are included at the ratio described above, removal efficiency of impurities in the alpha-olefin, in particular, the nitrogen-containing impurities may be dramatically improved. In addition, even in the case in which the impurities are present at a low concentration, the adsorption efficiency is excellent.

According to an exemplary embodiment of the present invention, the total content of the activated carbon and the alumina-zeolite composite may be 1 to 20 parts by weight, preferably 4 to 20 parts by weight, based on 100 parts by weight of the alpha-olefin. When the activated carbon and the alumina-zeolite composite are included at the contents described above, the purification ability of impurities in the alpha-olefin may be maximized.

According to an exemplary embodiment of the present invention, the alpha-olefin may be, specifically, for example, any one or a mixture of two or more selected from 1-butene, 1-pentene, 1-hexene, 4-methyl-1-pentene, 1-octene, 1-decene, 1-dodecene, and the like. Preferably, the alpha-olefin may be any one or a mixture of two or more selected from 1-hexene, 1-octene, and the like. More preferably, the alpha-olefin may be 1-octene.

When the purification method of the alpha-olefin according to the present invention is performed, the impurities present in the alpha-olefin may be dramatically purified. In particular, the impurities present in 1-octene may be removed with significantly improved purification efficiency.

According to an exemplary embodiment of the present invention, the impurities may include moisture, a hydrocarbon having 6 or fewer carbon atoms, a hydrocarbon having 10 carbon atoms, a hydrocarbon having 12 or more carbon atoms, nitrogen-containing impurities, and the like. Among them, the present invention may remove adsorption of the nitrogen-containing impurities well and the nitrogen-containing impurities may be specifically an amine-based compound. For example, the amine-based compound may include dioctylamine and the like. It is impossible to remove the material as such when it is adsorbed in the alumina-zeolite composite, and it is difficult to maintain a long-term purification ability by permanently decreasing a purification ability.

However, when the method of purifying an alpha-olefin according to the present invention is performed, a significantly improved purification ability as compared with the conventional purification ability may be implemented and also, a purification life span is improved, thereby allowing long-term use.

The method of purifying an alpha-olefin according to the present invention dramatically improved the problem of purification performance deterioration of an adsorbent, and an excellent impurity purification effect may be implemented. Thus, by producing or providing a high-purity alpha-olefin, the thus-produced alpha-olefin may implement high performance in various fields.

Another exemplary embodiment applies the method of purifying an alpha-olefin described above, and is a composition for purifying an alpha-olefin including: molded activated carbon having a specific surface area of 1,200 m²/g or more, an average particle diameter of 0.8 to 40 mm, and a pore volume of more than 0.6 cm³/g as measured by a nitrogen adsorption method, in which pores having a pore diameter of 2 nm or more account for 60% or more of the total pores; and an alumina-zeolite composite.

Since the physical properties and the contents of the activated carbon and the alumina-zeolite composite are as described above, description therefor will be omitted.

According to an exemplary embodiment of the present invention, the composition for purifying an alpha-olefin may be applied to any one or two or more positions selected from an introduction unit, a reaction unit, a circulation unit, a recovery unit, and the like in a process capable of performing purification. The shape provided is not particularly limited as long as a purification effect is expressed.

Specifically, according to an exemplary embodiment of the present invention, the composition for purifying an alpha-olefin may be applied during a poly-alpha-olefin polymerization reaction to which the alpha-olefin is added as a monomer or an ethylene oligomerization reaction in which the alpha-olefin is produced. By applying the composition during the reaction in which the alpha-olefin is provided or produced as described above, impurities may be purified, a high-purity alpha-olefin may be provided, and performance deterioration due to the impurities in various fields to be provided may be prevented. Furthermore, due to a long-term purification ability, a dramatic impurity purification effect may be implemented.

According to an exemplary embodiment of the present invention, the composition for purifying an alpha-olefin may be specifically, applied during a poly-alpha-olefin polymerization reaction or an ethylene oligomerization reaction, and specifically, may be applied to any one or two or more steps selected from before the reaction, during the reaction, and after the reaction. Specifically, for example, the purification method may be applied before the polymerization reaction of poly-alpha-olefin or after the ethylene oligomerization reaction. Preferably, in order to implement an excellent impurity purification effect, in particular, nitrogen-containing impurities, the composition may be applied before a poly-alpha-olefin polymerization reaction.

According to an exemplary embodiment of the present invention, for impurity purification, treatment may be performed by applying the composition for purifying an alpha-olefin once by mixing the activated carbon and the alumina-zeolite composite, or applying each sequentially.

Preferably, in order to sequentially apply each, the composition may be applied as a two agent-type composition including the activated carbon as a first agent and the alumina-zeolite composite as a second agent.

Specifically, in an exemplary embodiment, the composition may be provided so that pre-treatment is performed with the first agent and then post-treatment is performed with the second agent. For example, pre-treatment may be performed in an area including the first agent and then post-treatment may be performed in an area including the second agent. Otherwise, the first agent is added to perform pre-treatment and then is removed and the second agent is added to perform post-treatment, but it not limited as long as each of the first agent and the second agent may be sequentially treated.

According to an exemplary embodiment of the present invention, a time to purify impurities by the first agent and the second agent is not particularly limited, but the process may be independently of each other performed for 1 to 48 hours, preferably 5 to 30 hours.

When the composition is provided as the two agent-type composition as described above, the impurities are first purified by the activated carbon as a role of a guard bed, and then additional impurities are purified by alumina-zeolite composite, thereby having significantly improved impurity purification efficiency. Furthermore, a problem that the impurities are adsorbed to the inside of the alumina-zeolite composite and is not removed is prevented, thereby implementing a long-term purification ability.

According to an exemplary embodiment of the present invention, the composition for purifying an alpha-olefin has excellent selectivity to the nitrogen-containing impurities among the impurities in the alpha-olefin, and thus, a purification effect having further improved selectivity to the nitrogen-containing impurities may be implemented.

Hereinafter, the preferred Examples and Comparative Examples of the present invention will be described. However, the following Examples are only a preferred exemplary embodiment of the present invention, and the present invention is not limited thereto.

Measurement Method of Physical Properties

1. Crush Strength

The crush strength was measured in accordance with ASTM D3102-72, ASTM D4179-88a.

2. Measurement of Specific Surface Area (BET)

The specific surface area (BET) was calculated by a Brunauer-Emmett-Teller (BET) method by nitrogen adsorption-desorption and a Barret-Joyner-Halenda (BJH) method at a liquid nitrogen temperature (−196° C.).

3. Measurement of Purification Ability

For 100 parts by weight of a sample including 1,000 ppm of dioctyl amine, activated carbon was added to a batch reactor and then a purification treatment was performed at room temperature under normal pressure for 24 hours. Thereafter, an alumina-zeolite composite was added to the batch reactor and the purification treatment was performed at room temperature under normal pressure for 24 hours. To 10 g of the purified collected sample, (t-butylamido)dimethyl(tetramethylcyclopentadienyl)silanetitanium (IV) dichloride (4 µmol) and triphenylmethyl tetrakis(pentafluorophenyl) borate and triisobutylaluminum as a cocatalyst were added and synthesis was performed at room temperature under normal pressure. After 10 minutes, a rise in reaction temperature was measured and converted into an impurity removal rate as follows. When calculating the impurity removal rate, a correction was made by applying an exothermic temperature of the collected sample which was not purified.

Impurity removal rate={(exothermic temperature after purification with the corresponding adsorbent−exothermic temperature before purification)/(exothermic temperature of completely purified collected sample−exothermic temperature before purification)}×100

4. Pore Volume and Diameter

The measurement principle of BET is as follows: when in a closed container, gas is adsorbed or desorbed to a sample depending on a partial pressure of gas in the container without a change in other conditions, a change in the partial pressure of gas in the container is measured to calculate an adsorbed amount and the specific surface area of the sample may be measured. For measuring the mesopore size, a Barrett-Joyner-Halenda (BJH) method based on a Kelvin equation was used for calculation. In addition, for measuring the mesopore volume, an amount of nitrogen adsorbed at a relative pressure of 0.95 or less was used for analysis.

Example 1

For 100 parts by weight of a sample including 1,000 ppm of dioctyl amine, 1 part by weight of activated carbon was added into a batch reactor and then a purification treatment was performed at room temperature under normal pressure for 24 hours. Thereafter, 5 parts by weight of an alumina-zeolite composite was added into the batch reactor, and the purification treatment was performed at room temperature under normal pressure for 24 hours.

Here, the activated carbon was a granule form having a specific surface area of 1,485 $m^2/g$ and a particle diameter of 95% or more of 0.85 to 1.7 mm, had a pore volume of more than 0.6 $cm^3/g$ as measured by a nitrogen adsorption method, and had pores having a particle diameter of 2 nm or more accounting for 60.1% of the total pores.

As the alumina-zeolite composite, a bead form containing 70 wt % of alumina and 30 wt % of zeolite, having a crush strength of 33 N, and a particle diameter of 1.4 to 2.8 mm was used.

Example 2

The process was performed in the same manner as in Example 1, except that 1 part by weight of the activated carbon and 3 parts by weight of the alumina-zeolite composite were added.

Example 3

The process was performed in the same manner as in Example 1, except that 1 part by weight of the activated carbon and 20 parts by weight of the alumina-zeolite composite were added.

Example 4

The process was performed in the same manner as in Example 1, except that the alumina-zeolite composite was first added and then the activated carbon was added.

Example 5

The process was performed in the same manner as in Example 1, except that the activated carbon having a specific surface area of 1,460 $m^2/g$, a pore volume of more than 0.6 $cm^3/g$ as measured by a nitrogen adsorption method, and pores having a pore diameter of 2 nm or more accounting for 61.1% of the total pores, which was produced by a production method which is different from the production method of the conventional activated carbon, was used.

Comparative Example 1

The process was performed in the same manner as in Example 1, except that the activated carbon was not used.

Comparative Example 2

The process was performed in the same manner as in Example 1, except that the alumina-zeolite composite was not used.

Comparative Example 3

The process was performed in the same manner as in Example 1, except that the activated carbon having a specific surface area of 1,445 $m^2/g$, a pore volume of more than 0.6 $cm^3/g$ as measured by a nitrogen adsorption method, and pores having a pore diameter of 2 nm or more accounting for 17.1% of the total pores, was used.

Comparative Example 4

The process was performed in the same manner as in Example 1, except that the activated carbon having a specific surface area of 746 $m^2/g$, a pore volume of more than 0.6 $cm^3/g$ as measured by a nitrogen adsorption method, and pores having a pore diameter of 2 nm or more accounting for 20.5% of the total pores, was used.

Comparative Example 5

The process was performed in the same manner as in Example 1, except that the activated carbon having a specific surface area of 1,166 $m^2/g$, a pore volume of more than 0.6 $cm^3/g$ as measured by a nitrogen adsorption method, and pores having a pore diameter of 2 nm or more accounting for 40.5% of the total pores, was used.

Comparative Example 6

The process was performed in the same manner as in Example 1, except that the activated carbon having a specific surface area of 1,249 $m^2/g$, a pore volume of more than 0.6 $cm^3/g$ as measured by a nitrogen adsorption method, and pores having a pore diameter of 2 nm or more accounting for 28.0% of the total pores, was used.

Comparative Example 7

The process was performed in the same manner as in Example 1, except that the activated carbon having a specific surface area of 1,505 $m^2/g$, a pore volume of more than 0.6 $cm^3/g$ as measured by a nitrogen adsorption method, and pores having a pore diameter of 2 nm or more accounting for 63.0% of the total pores, which is a powder form, was used.

Comparative Example 8

The process was performed in the same manner as in Example 1, except that the activated carbon had a specific surface area of 1,237 $m^2/g$, a pore volume of more than 0.6 $cm^3/g$ as measured by a nitrogen adsorption method, and pores having a pore diameter of 2 nm or more accounting for 61.7% of the total pores, which is a powder form, was used.

Purification ability measurement was performed using the samples purified in the Examples and the Comparative Examples and the impurity removal rates are shown in the following Table 1.

TABLE 1

| | Impurity removal rate |
|---|---|
| Example 1 | 97.1% |
| Example 2 | 73.2% |
| Example 3 | 99.0% |
| Example 4 | 72.7% |
| Example 5 | 88.3% |
| Comparative Example 1 | 27.8% |
| Comparative Example 2 | 22.0% |
| Comparative Example 3 | 3.41% |
| Comparative Example 4 | 22.0% |
| Comparative Example 5 | 46.8% |
| Comparative Example 6 | 39.0% |
| Comparative Example 7 | 29.3% |
| Comparative Example 8 | 29.8% |

As shown in Table 1, it was confirmed that when the method of purifying an alpha-olefin according to the present invention was performed, an impurity purification effect was significantly good. In particular, it was confirmed that the impurity removal rate was 85% or more, which is 3 times or more the purification efficiency of the Comparative Example.

It was confirmed that the alpha-olefin purified by the method of purifying an alpha-olefin according to the present invention had impurities purified to less than the detection limit even in the case of including from a low concentration to a high concentration of impurities of 10 to 500 ppm.

Furthermore, upon comparison of Examples 1 and 5, it was confirmed that when the alpha-olefin was treated with activated carbon and then the alumina-zeolite composite, a further improved purification effect was able to be implemented.

In addition, upon comparison of Examples 1 to 3, it was confirmed that when the activated carbon and the alumina-zeolite composite were included at a weight ratio of 1:5 to 1:20, a purification ability was better than the case including the activated carbon and the alumina-zeolite composite at a weight ratio of 1:3.

As in Example 5, it was confirmed that even when using activated carbon having a specific surface area of 1,200 $m^2$/g or more, a pore volume of more than 0.6 $cm^3$/g as measured by a nitrogen adsorption method, and pores having a pore diameter of 2 nm or more accounting for 60% or more of the total pores, that was produced by a different production method, a similar purification ability was obtained.

As in Comparative Examples 1 and 2, when any one of the activated carbon and the alumina-zeolite composite was not included, it was confirmed that the purification ability was at an insignificant level. In particular, since in Comparative Example 1, impurities were strongly adsorbed to the inside of the alumina-zeolite composite during the purification process and life shortening occurs to decrease durability, it was difficult to implement a long-term effect.

As in Comparative Example 3 to 6, when using a constitution in which the physical properties and the shape of the activated carbon and the alumina-zeolite composite according to the present invention were different, it was confirmed that the effect was insignificant so as not to reach the purification effect of the present invention.

As in Comparative Examples 7 and 8, when using the activated carbon having a pore volume of more than 0.6 $cm^3$/g as measured by a nitrogen adsorption method and pores having a pore size of 2 nm or more accounting for 60% or more of the total pores, but in a powder form, it was confirmed that the effect was insignificant so as not to reach the purification effect of the present invention.

The method of purifying an alpha-olefin according to the present invention has excellent purification selectivity particularly to nitrogen-containing impurities among impurities in the alpha-olefin.

In addition, the composition for purifying an alpha-olefin according to the present invention has an excellent impurity purification ability even at a low concentration.

Hereinabove, although the present invention has been described by the specific matters and specific exemplary embodiments, they have been provided only for assisting in the entire understanding of the present invention. Therefore, the present invention is not limited to the exemplary embodiments, and various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A method of purifying an alpha-olefin, wherein impurities are removed by a combination of
    molded activated carbon having a specific surface area of 1,200 $m^2$/g or more, an average particle diameter of 0.8 to 40 mm, and a pore volume of more than 0.6 $cm^3$/g as measured by a nitrogen adsorption method, in which pores having a pore diameter of 2 nm or more account for 60% or more of total pores; and
    an alumina-zeolite composite.

2. The method of purifying an alpha-olefin of claim 1, wherein the method of purifying an alpha-olefin is performed during a poly-alpha-olefin polymerization reaction or an ethylene ol i gom eri zati on reaction.

3. The method of purifying an alpha-olefin of claim 2, wherein the method of purifying an alpha-olefin is performed during the poly-alpha-olefin polymerization reaction.

4. The method of purifying an alpha-olefin of claim 1, wherein the method of purifying an alpha-olefin includes treatment with the activated carbon and then treatment with the alumina-zeolite composite sequentially.

5. The method of purifying an alpha-olefin of claim 1, wherein the activated carbon; and the alumina-zeolite composite are included at a weight ratio of 1:1 to 1:20.

6. The method of purifying an alpha-olefin of claim 1, wherein the alumina-zeolite composite includes 50 to 95 wt % of alumina and 5 to 50 wt % of zeolite.

7. The method of purifying an alpha-olefin of claim 1, wherein the alpha-olefin is any one or a mixture of two or more selected from 1-butene, 1-pentene, 1-hexene, 4-methyl-1-pentene, 1-octene, 1-decene, and 1-dodecene.

8. The method of purifying an alpha-olefin of claim 7, wherein the alpha-olefin is any one selected from 1-hexene and 1-octene or a mixture thereof.

9. The method of purifying an alpha-olefin of claim 1, wherein the impurities are an amine-based compound.

10. A composition for purifying an alpha-olefin, the composition comprising:
    molded activated carbon having a specific surface area of 1,200 $m^2$/g or more, an average particle diameter of 0.8 to 40 mm, and a pore volume of more than 0.6 $cm^3$/g as measured by a nitrogen adsorption method, in which pores having a pore diameter of 2 nm or more account for 60% or more of total pores; and
    an alumina-zeolite composite.

11. The composition for purifying an alpha-olefin of claim 10, wherein the composition for purifying an alpha-olefin includes the activated carbon as a first agent and the alumina-zeolite composite as a second agent.

* * * * *